United States Patent [19]
Rosselson et al.

[11] Patent Number: 6,073,492
[45] Date of Patent: Jun. 13, 2000

[54] ULTRASONIC SENSOR FOR VERY HIGH TEMPERATURES AND PRESSURES

[75] Inventors: Boris S. Rosselson; Alexander J. Esin, both of Buffalo Grove; Lawrence J. Jones, West Dundee, all of Ill.

[73] Assignee: Kay-Ray Sensall, Inc., Mount Prospect, Ill.

[21] Appl. No.: 09/215,600

[22] Filed: Dec. 17, 1998

[51] Int. Cl.[7] .................................................. G01N 29/02
[52] U.S. Cl. ........................... 73/644; 73/1.83; 73/290 V
[58] Field of Search .................................. 73/644, 290 V, 73/32 R, 1.82, 1.83, 610, 612, 590

[56] References Cited

U.S. PATENT DOCUMENTS

| | | | |
|---|---|---|---|
| 5,159,838 | 11/1992 | Lynnworth | 73/644 |
| 5,269,188 | 12/1993 | Esin et al. | 73/610 |
| 5,428,984 | 7/1995 | Jones et al. | 73/1.83 |
| 5,708,209 | 1/1998 | Stiffler et al. | 73/644 |

OTHER PUBLICATIONS

A.B. Gillespie, M.O. Deighton, R.B. Pike and R.D. Watkins, "A New Ultrasonic Technique for the Measurement of Liquid Level,", pp. 13–17, *Ultrasonic*, Jan. 1982.

R.D. Watkins, M.O. Deighton, A.B. Gillespie and R.B. Pike, "A Proposed Method for Generating and Receiving Narrow Beams of Ultrasound in the Fast Reactor Liquid Sodium Environment," *Ultrasonics* Jan., 1982, pp. 7–12.

*Primary Examiner*—John E. Chapman
*Attorney, Agent, or Firm*—Westman, Champlin & Kelly, P.A.

[57] ABSTRACT

An ultrasonic sensor includes an ultrasonic transmitter, an ultrasonic receiver and a support structure. First and second elongated tubes are mechanically coupled to and extend from the support structure. A first elongated waveguide is operably coupled to the ultrasonic transmitter and extends through the support structure and a bore in the first tube. The first waveguide is acoustically isolated from the support structure and first tube except at a distal portion of the first waveguide. A second elongated waveguide is operably coupled to the ultrasonic receiver and extends through the support structure and a bore in the second tube. The second waveguide is acoustically isolated from the support structure and the second tube except at a distal portion of the second waveguide. A measurement gap is located between the distal portions of the first and second waveguides.

14 Claims, 2 Drawing Sheets

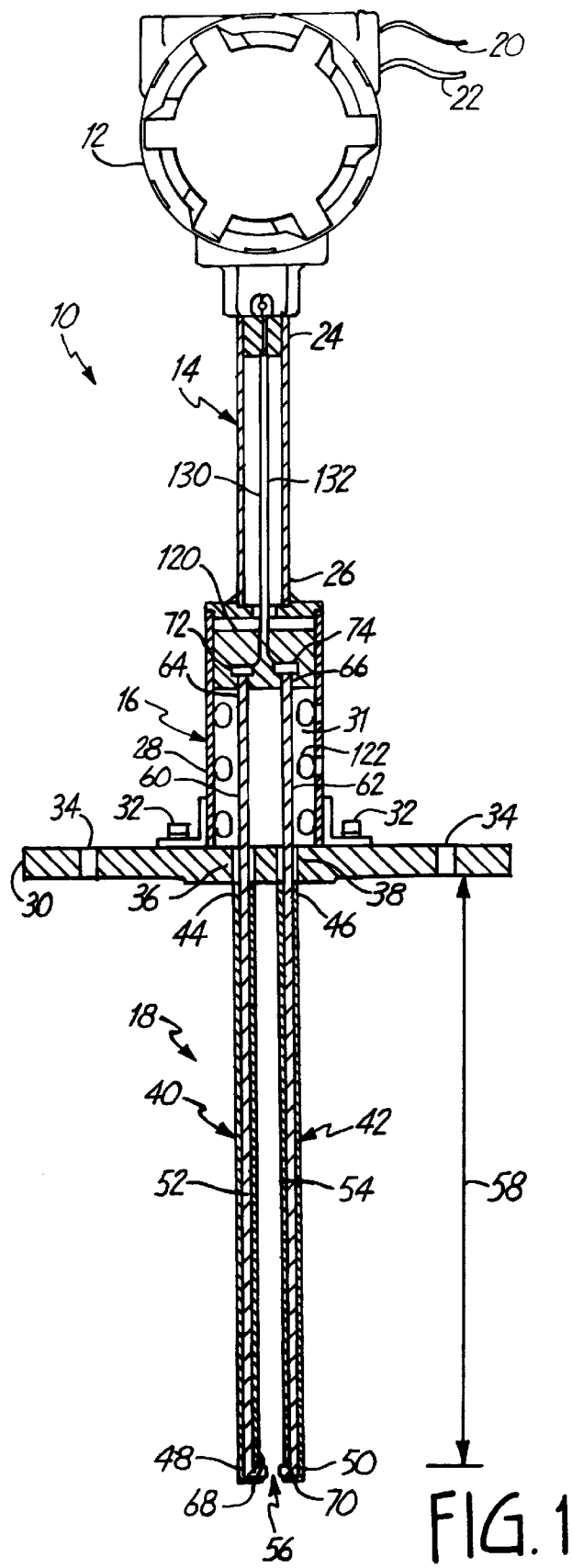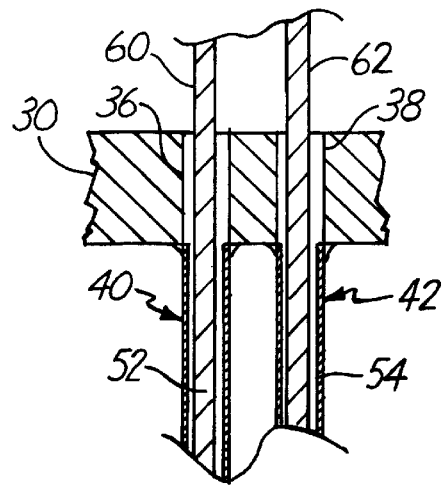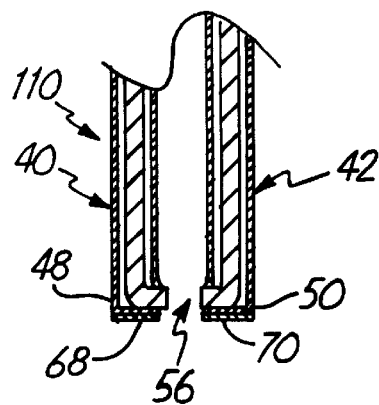
FIG. 1
FIG. 2

ULTRASONIC SENSOR FOR VERY HIGH TEMPERATURES AND PRESSURES

BACKGROUND OF THE INVENTION

The present invention relates to ultrasonic sensors for measuring physical properties of materials within a defined space, and relates more particularly to a time gate ultrasonic sensor system for very high temperatures and pressures.

Various ultrasonic distance and level measuring sensors are known. For example, ultrasonic sensors have been used as point level switches for detecting high and low material levels in a process container. Industrial process applications include petroleum, chemical, pulp and paper, mining and materials, oil and gas applications, among others. In these applications, a point level switch is often the last means of detecting an overflow or underflow condition. Safety, measurement accuracy, and sensor integrity are critical.

Esin et al. U.S. Pat. No. 5,269,188 discloses a continuous self-test time gate ultrasonic sensor system which measures presence or density of a process material within a defined space. The sensor includes a transmit transducer and receive transducer which are connected to opposite sides of a U-shaped support structure for transmitting and receiving ultrasonic signals across the defined space. The ultrasonic signals include a main waveform which travels across the defined space and a self-test waveform which travels along the support structure. The sensor senses the physical property of the material within the defined space as a function of whether the main waveform is received within the main time window. The sensor performs a self-test during each measurement cycle by sensing whether the self-test waveform is received during a self-test time window which is different from the main time window. For a correctly operating sensor, the self-test waveform should be present during each measurement cycle.

A deficiency of this type of ultrasonic sensor is that the transmit and receive transducers are bonded to the inside of the sensor body which is submerged in the process to be measured. For piezoceramic transducers, for example, the maximum temperature of the process in which this sensor can be used is therefore limited to a temperature that is below the Curie point of the transducers to avoid depolarization and other damage to the transducers or their bonds to the support structure. In many applications, the process to be measured is hazardous, such as with flammable or explosive materials, and may be under very high temperatures and pressures. An ultrasonic sensor capable of operating under very high temperature and pressures is desired.

SUMMARY OF THE INVENTION

The ultrasonic sensor of the present invention includes an ultrasonic transmitter, an ultrasonic receiver and a support structure. First and second elongated tubes are mechanically coupled to and extend from the support structure. A first elongated waveguide is operably coupled to the ultrasonic transmitter and extends through the support structure and a lumen (or bore) in the first tube. The first waveguide is acoustically isolated from the support structure and first tube except at a distal portion of the first waveguide. The distal portion of the first waveguide is acoustically coupled to the distal portion of the first tube. A second elongate waveguide is operably coupled to the ultrasonic receiver and extends through the support structure and a lumen in the second tube. The second waveguide is acoustically isolated from the support structure and the second tube except at a distal portion of the second waveguide. The distal portion of the second waveguide is acoustically coupled to the distal portion of the second tube. A measurement gap is located between the distal portions of the first and second waveguide.

Another aspect of the present invention relates to an ultrasonic sensor which includes an ultrasonic transmitter, an ultrasonic receiver and a support structure. First and second elongated waveguide supports are coupled to and extend from the support structure. A first elongated waveguide is operably coupled to the ultrasonic transmitter and extends through the support structure and along the first waveguide support. The first waveguide is acoustically isolated from the support structure and the first waveguide support from the ultrasonic transmitter to a first location that is opposite to the support structure relative to the ultrasonic transmitter. The first waveguide is acoustically coupled to the first waveguide support at the first location. A second elongated waveguide is operably coupled to the ultrasonic receiver and extends along the second waveguide support. The second waveguide is acoustically isolated from the support structure and the second waveguide support from the ultrasonic receiver to a second location that is opposite to the support structure relative to the ultrasonic receiver. The second waveguide is acoustically coupled to the second waveguide support at the second location. A measurement gap is defined between the first and second waveguides.

Yet another aspect of the present invention relates to an ultrasonic sensor which includes a support structure for coupling to a process to be measured and having a process isolated side and a process exposed side. An ultrasonic transmitter and an ultrasonic receiver are positioned on the process isolated side. A waveguide apparatus guides ultrasonic signals through a main waveform travel path from the ultrasonic transmitter to a measurement gap on the process exposed side and from the measurement gap to the ultrasonic receiver. A waveguide support apparatus supports the waveguide apparatus on the process exposed side and isolates the process isolated side from the process exposed side. The waveguide support apparatus is coupled to the waveguide apparatus so as to define a self-test travel path for the ultrasonic signals from the ultrasonic transmitter to the ultrasonic receiver, wherein the self-test travel path is different from and longer than the main waveform travel path.

BRIEF DESCRIPTION OF THE DRAWINGS

FIG. 1 is a partial cross-sectional view of an ultrasonic sensor according to one embodiment of the present invention.

FIG. 2 is a fragmentary cross-sectional view of a flange, waveguide support tubes and waveguides within the sensor shown in FIG. 1.

DETAILED DESCRIPTION OF THE PREFERRED EMBODIMENTS

Figure 3:
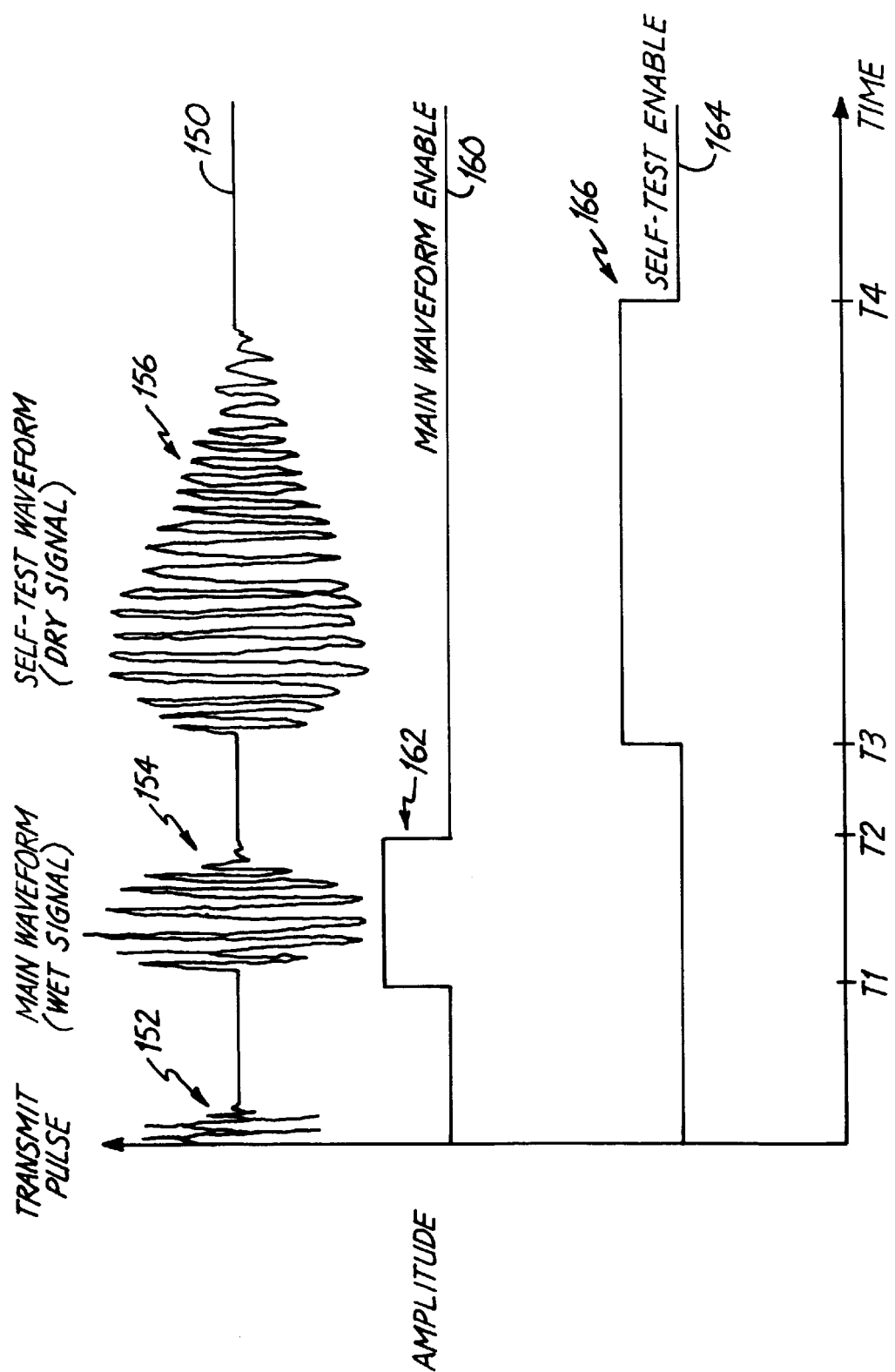
FIG. 3 is a waveform diagram showing various waveforms in the sensor shown in FIG. 1 over time.

FIG. 1 is a partial cross-sectional view of an ultrasonic sensor or point level switch according to one embodiment of the present invention. The sensor is able to determine a property or presence of a material across a measuring gap at very high temperatures (up to the temperature of molten metals) and at very high pressures. Also, the sensor construction defines a main ultrasonic signal travel path through the measuring gap and a separate self-test ultrasonic signal travel path through the support structure to provide a continuous self-test of sensor integrity during each measurement cycle.

Sensor 10 includes electronics housing 12, thermal isolation neck 14, support structure 16 and process insertion portion 18. Electronics housing 12 contains a measurement circuit for initiating a measurement, processing measurement results and communicating the measurement results to a remote device, such as a central control room or a valve, for example.

Electronics housing 12 is threaded onto a first end 24 of thermal isolation neck 14, and a second end 26 of neck 14 is welded to support structure 16. Support structure 16 includes an upper portion 28 and a flange 30 which together define a housing with an internal cavity 31. Upper portion 28 and flange 30 are bolted together with bolts 32. Flange 30 is, in-turn, bolted or otherwise connected through mounting holes 34 to the top of a tank or similar container (not shown) which contains the material to be measured. Flange 30 can form a process connecting flange or can form part of any one of a variety of other process connectors, such as an NPT fitting. Flange 30 includes a pair of holes 36 and 38.

Process insertion portion 18 includes waveguide support tubes 40 and 42 which extend downward from flange 30. Tubes 40 and 42 have proximal ends 44 and 46, distal ends 48 and 50, and internal lumens (or bores) 52 and 54, respectively. Proximal ends 44 and 46 are attached to flange 30 such that lumens 52 and 54 are coaxial with flange holes 36 and 38, respectively. In one embodiment, the proximal ends 44 and 46 are welded to the bottom of flange 30 to form a hermetic seal about flange holes 36 and 38. The hermetic seal isolates internal cavity 31 relative to the exterior surfaces of tubes 40 and 42 and thus the process conditions of the tank (not shown). The distal ends 48 and 50 of tubes 40 and 42 are separated from one another by a measurement gap 56.

Tubes 40 and 42 have a length 58 which is selected for the particular application in which the sensor is used. For example, length 58 may be selected to define the distance from the top of the tank to a desired detection point in the tank. The desired detection point may be a high or low level point in the tank.

Sensor 10 further includes waveguides 60 and 62 having proximal ends 64 and 66 and distal ends 68 and 70, respectively. Waveguide 60 extends through flange hole 36 and lumen 52 of tube 40. Waveguide 62 extends through flange hole 38 and lumen 54 of tube 42. A transmit transducer (e.g. crystal) 72 is bonded to the proximal end 64 of waveguide 60, within internal cavity 31. A receive transducer (e.g. crystal) 74 is bonded to the proximal end 66 of waveguide 62, within internal cavity 31. The distal end 68 of waveguide 60 is attached to the distal end 48 of tube 40. The distal end 70 of waveguide 62 is attached to the distal end 50 of tube 42. In one embodiment, the distal ends 68 and 70 of waveguides 60 and 62 are welded about the distal ends 48 and 50 of tubes 40 and 42 to form a hermetic seal which isolates lumens 52 and 54 from the process. The distal ends 68 and 70 of waveguides 60 and 62 are bent such that they are coaxially aligned with and separated from one another across measurement gap 56.

Waveguides 60 and 62 are completely free of direct mechanical contact with flange 30 and tubes 40 and 42, except at their distal ends 68 and 70. This mechanical isolation is shown in greater detail in FIG. 2. FIG. 2 is a fragmentary cross-sectional view of flange 30, tubes 40 and 42 and waveguides 60 and 62. Waveguides 60 and 62 pass through holes 36 and 38 of flange 30 without contacting flange 30 or tubes 40 and 42. The welds between waveguides 60 and 62 and their respective tubes 40 and 42 define acoustic couplings between waveguides 60 and 62 and tubes 40 and 42.

Waveguides 60 and 62 extend through tubes 40 and 42 and are spaced from the internal surfaces of tubes 40 and 42 in such a way that there is no direct contact with tubes 40 and 42, except at their distal ends 68 and 70. Waveguides 60 and 62 are thus acoustically isolated from flange.30 and tubes 40 and 42, except at distal ends 68 and 70. Alternatively, waveguides 60 and 62 can be attached to tubes 40 and 42 at other locations along a distal portion 110 of the waveguides, which are selected to provide a desired length of the self-test waveform travel path as is also discussed in more detail below.

Referring back to FIG. 1, internal cavity 31 is at least partially filled or "backpotted" with an acoustically isolating material 120 to prevent wobbling of waveguides 60 and 62. The material 120 supports proximal ends 64 and 66 of waveguides 60 and 62 and transducers 72 and 74 relative to support structure 16. Material 120 maintains acoustic isolation between transmit and receive transducers 72 and 74, support structure 16 and waveguides 60 and 62. In one embodiment, material 120 includes an adhesive material such as Eccolite 4640 which is manufactured by Emerson & Cuming Specialty Polymers of London, England. Other potting material can also be used as long as the material sufficiently isolates the transducers from each other and from and waveguides from the support structure. In one embodiment, the material preferably attenuates the ultrasonic signals passing between the waveguides and, also, to support structure 16 by at least 100 db.

With the structure shown in FIG. 1, the transmit and receive transducers 72 and 74 are positioned outside the process relative to flange 30 and are hermetically sealed with respect to the process. This significantly extends the temperatures and pressures to which sensor 10 can be exposed and thereby enables sensor 10 to be used in more extreme process applications. For example, if flange 30, tubes 40 and 42 and waveguides 60 and 62 are made of metal, then sensor 10 would be capable of handling process temperatures up to the temperature of molten metal. To provide additional cooling and ventilation, upper portion 28 of support structure 16 is preferably perforated with holes 122.

Transmit transducer 72 is electrically coupled to the measurement circuitry within electronics housing 12 through coaxial cable 130. Similarly, receive transducer 74 is electrically coupled to the measurement circuitry within electronics housing 12 through coaxial cable 132.

During a measurement cycle, an oscillator in electronics housing 12 periodically applies a transmit pulse to transmit transducer 72 over cable 130. The transmit pulse energizes (or excites) transducer 72 causing the transducer to resonate at its natural frequency and emanate an ultrasonic signal. The ultrasonic signal travels along two different paths from transmit transducer 72 to receive transducer 74.

In the main waveform travel path, the ultrasonic signal travels down waveguide 60 to measurement gap 56, across measurement gap 56 to waveguide 62 (when process material is present in the gap) and up waveguide 62 to receive transducer 74. Receive transducer 74 converts the received ultrasonic signal to an electrical signal which is provided to the measurement circuitry in housing 12 through cable 132.

The measurement circuitry in housing 12 detects the presence or absence of material within gap 56 as a function of whether the main waveform is received by receive transducer 74 within a main time window. The main time window is measured relative to the transmit pulse provided to the transmit transducer.

Absorption of the ultrasonic signal crossing measurement gap 56 is inversely related to the density of the material in the gap. Also, ultrasonic signals travel faster in liquids than in air and travel faster in solids than in liquids. Therefore, when gap 56 is void of material, the main waveform is significantly attenuated and delayed in time as compared to when there is material present in the gap. Absorption in gap 56 is particularly great at high frequencies such as above several kilohertz and higher. As a result, receipt of the main waveform within the main time window and with at least a threshold amplitude indicates the presence of a material within gap 56.

In the self-test travel path, the ultrasonic signal generated by transmit transducer 74 travels down waveguide 60, from proximal end 64 to distal end 68, from distal end 68 across the acoustic coupling to distal end 48 of tube 40, up tube 40 from distal end 48 to proximal end 44, and from proximal end 44 to flange 30. The ultrasonic signal then travels from flange 30 to proximal end 46 of tube 42, down tube 42 to distal end 50, from distal end 50 of tube 42 across the acoustic coupling to distal end 70 of wave guide 62, up waveguide 62 to proximal end 66, and from proximal end 66 to receive transducer 74. The ultrasonic signal that travels along the self-test travel path is referred to as a "self-test waveform".

With a properly functioning sensor, the self-test waveform should always be received by receive transducer 74 after each transmitted pulse. The absence of the self-test waveform or a reduction in the signal level of the self-test waveform is an indication of a malfunction or damage to the sensor and the sensor's inability to make a measurement. The measurement circuitry in electronics housing detects the presence or absence of the self-test waveform within a self-test time window which is measured relative to the transmit pulse provided to transmit transducer 72. The self-test time window is temporally separated from the main time window.

Although ultrasonic signals travel faster in metal than in liquid, the self-test travel path is much longer than the main waveform travel path. The long self-test travel path is created by maintaining acoustic isolation between waveguides 60 and 62 and tubes 40 and 42, from transducers 72 and 74 to the distal ends of waveguides 60 and 62. With the long self-test travel path, the self-test waveform arrives at receive transducer 74 significantly later in time than the main waveform. This prevents the self-test waveform from overlapping and interfering with the main waveform. Since only the main waveform arrives within the main time window, the main waveform has a higher and more consistent "wet/dry" ratio. In other words, the amplitude of the main waveform is minimized when there is no material within gap 56 as compared to the amplitude of the main waveform when there is material present in gap 56.

Increasing the "wet/dry" ratio significantly improves quality and reliability of a measurement. This is particularly important for applications where the ultrasonic signal being propagated through waveguides 60 and 62 and gap 56 becomes dramatically attenuated by the process material present in the gap. The attenuation also depends on operating frequency. The frequency range of the oscillator in electronics housing 12 is determined by the resonant frequencies of transmit transducer 74 and receive transducer 74, the lengths of waveguides 60 and 62 and the material used for forming waveguides 60 and 62.

The measurement electronics used in electronics housing 12 for generating the transmit pulses, and detecting the presence or absence of the main waveform and the self-test waveform within the main waveform time window and the self-test time window are described in more detail in Esin et al. U.S. Pat. No. 5,269,188, which is hereby incorporated by reference. Other circuits can also be used.

FIG. 3 is a waveform diagram showing various waveforms in sensor lo over time. Line 150 represents the ultrasonic signals generates by transmit transducer 72 and received by receive transducer 74 during one measurement cycle, which have been superimposed on one another. Waveform 152 in line 150 represents the ultrasonic signal generated by transmit transducer 72 in response to the transmit pulse supplied by the oscillator. Waveform 154 in line 150 represents the main waveform received by receive transducer 74 which traveled through the main waveform travel path (i.e. through waveguide 60, gap 56 and waveguide 62). Waveform 156 in line 150 represents the self-test waveform received by receive transducer 74 which traveled through the self-test travel path (i.e. through waveguide 60, tube 40, flange 30, tube 42 and waveguide 62). Self-test waveform 156 arrives at receive transducer 74 later in time than main waveform 154.

Line 160 represents a main waveform enable signal which goes active at time T1 and inactive at time T2 to define a main waveform time window 162. Between times T1 and T2, main waveform enable signal 160 enables the measurement circuitry to monitor the output of receive transducer 74 for the presence or absence of main waveform 154 The presence of main waveform 154 within main waveform time window 162 indicates the presence of the process material within gap 56 (shown in FIG. 1). The absence of main waveform 154 within main waveform time window 162 indicates the absence of the process material within gap 56 or no signal due to failure of the transmit or receive transducers 72 and 74.

Line 166 represents a self-test enable signal which goes active at time T3 and inactive at time T4 to define a self-test time window 166. Between times T3 and T4, self-test enable signal 164 enables the measurement circuitry to monitor the output of receive transducer 74 for the presence or absence of self-test waveform 156. The presence of self-test waveform 156 within self-test time window 166 indicates proper functioning of sensor 10. The absence of self-test waveform 156 within self-test time window 166 indicates a malfunction in sensor 10 and that the presence or absence of the main, waveform enable signal cannot be relied upon to determine a wet or dry condition in the gap.

The continuous self-test function allows the sensor system of the present invention to make a judgement as to whether the sensor is capable of making a measurement. If not, the sensor system can trigger a warning or other alert that can be monitored by the overall control system. This is particularly important since ultrasonic level sensors such as point level switches are often used to provide a last warning of a potential overflow condition in a process tank. Also, the sensor system of the present invention is extremely reliable since the transmit and receive transducers are isolated from the process by the waveguide support tubes and the flange.

As mentioned above, the acoustic coupling between waveguides 60 and 62 and their respective tubes 40 and 42 can be placed at any selected location along distal portion 110 of the waveguides. The particular location of the acoustic coupling depends on the lengths of waveguides 60 and 62 and tubes 40 and 42, the operating frequency of the oscillator and the degree of time separation desired between main waveform 154 and self-test waveform 156 that are received by receive transducer 74. Structural factors may also affect the desired location of the acoustic coupling.

Although the present invention has been described with reference to preferred embodiments, workers skilled in the art will recognize that changes may be made in form and detail without departing from the spirit and scope of the invention. For example, tubes 40 and 42 and waveguides 60 and 62 can have any desired cross-sectional shape, such as circular or rectangular. Also, tubes 40 and 42 can extend through holes 36 and 38 and into internal cavity 31 of support structure 16 for any desired length. Tubes 40 and 42 and waveguides 60 and 62 can be formed of any suitable material such as metal or plastic depending upon the particular application in which the sensor is used.

What is claimed is:

1. An ultrasonic sensor comprising:
   an ultrasonic transmitter;
   an ultrasonic receiver;
   a support structure;
   first and second elongated tubes which are mechanically coupled to and extend from the support structure;
   a first elongated waveguide which is operably coupled to the ultrasonic transmitter and extends through the support structure and a bore in the first tube, wherein the first waveguide is acoustically isolated from the support structure and the first tube except at a distal portion of the first tube;
   a first acoustic coupling between a distal portion of the first waveguide and the distal portion of the first tube;
   a second elongated waveguide which is operably coupled to the ultrasonic receiver and extends through the support structure and a bore in the second tube, wherein the second waveguide is acoustically isolated from the support structure and the second tube except at a distal portion of the second tube;
   a second acoustic coupling between a distal portion of the second waveguide and the distal portion of the second tube; and
   a measurement gap located between the distal portions of the first and second waveguides.

2. The ultrasonic sensor of claim 1 wherein:
   the support structure comprises an internal cavity and first and second holes which extend to the internal cavity;
   the first tube is attached to the support structure such that the bore of the first tube is coaxial with the first hole;
   the second tube is attached to the support structure such that the bore of the second tube is coaxial with the second hole; and
   the first and second waveguides have proximal ends, which are attached to the ultrasonic transmitter and the ultrasonic receiver, respectively, within the internal cavity, and extend through the first and second holes, respectively, and into the bores of the first and second tubes without contacting the support structure or the first and second tubes.

3. The ultrasonic sensor of claim 2 wherein the first and second tubes are hermetically sealed about the first and second holes, respectively, such that the internal cavity is sealed with respect to external surfaces of the first and second tubes.

4. The ultrasonic sensor of claim 2 wherein the internal cavity is at least partially filled with an acoustically isolating material which supports the proximal ends of the first and second waveguides relative to the support structure while maintaining acoustic isolation between the first and second waveguides and the support structure.

5. The ultrasonic sensor of claim 2 wherein the distal portions of the first and second elongated waveguides are mechanically attached to the distal portions of the first and second tubes, respectively, and wherein the first and second waveguides are free of mechanical contact with the first and second tubes from the first and second acoustic couplings to the internal cavity of the support structure.

6. The ultrasonic sensor of claim 5 wherein the distal portions of the first and second tubes are hermetically sealed about the distal portions of the first and second waveguides, respectively, such that the bores of the first and tubes and the internal cavity are sealed with respect to external surfaces of the first and second tubes.

7. The ultrasonic sensor of claim 1 wherein the first and second waveguides extend parallel to one another from the support structure toward the measurement gap and are coaxially aligned with and separated from one another across the measurement gap.

8. The ultrasonic sensor of claim 1 wherein:
   the support structure the support structure comprises a housing with an internal cavity;
   the first and second waveguides are operably coupled to the ultrasonic transmitter and receiver, respectively within the internal cavity; and
   the housing comprises a plurality of ventilation perforations.

9. The ultrasonic sensor of claim 1 and further comprising:
   a main ultrasonic signal travel path from the ultrasonic transmitter, down the first waveguide to the measurement gap, across the measurement gap from the first waveguide to the second waveguide, and up the second waveguide to the ultrasonic receiver; and
   a self-test ultrasonic signal travel path from the ultrasonic transmitter, down the first waveguide to the distal portion of the first waveguide, across the first acoustic coupling to the distal portion of the first tube, up the first tube to the support structure, from the support structure to the second tube, down the second tube to the distal portion of the second tube, across the second acoustic coupling to the distal portion of the second waveguide, and up the second waveguide to the ultrasonic receiver.

10. An ultrasonic sensor comprising:
    an ultrasonic transmitter;
    an ultrasonic receiver;
    a support structure;
    first and second elongated waveguide supports which are coupled to and extend from the support structure;
    a first elongated waveguide which is operably coupled to the ultrasonic transmitter and extends through the support structure and along the first waveguide support, wherein the first waveguide is acoustically isolated from the support structure and the first waveguide support from the ultrasonic transmitter to a first location that is opposite to the support structure relative to the ultrasonic transmitter, and is acoustically coupled to the first waveguide support at the first location;
    a second elongated waveguide which is operably coupled to the ultrasonic receiver and extends along the second waveguide support, wherein the second waveguide is acoustically isolated from the support structure and the second waveguide support from the ultrasonic receiver to a second location that is opposite to the support structure relative to the ultrasonic receiver, and is acoustically coupled to the second waveguide support at the second location; and a measurement gap defined between the first and second waveguides.

11. The ultrasonic sensor of claim 10 wherein the support structure comprises an internal cavity in which the first and second waveguides are coupled to the ultrasonic transmitter and receiver, respectively, and wherein the first and second waveguides are mechanically coupled to the first and second waveguide supports at the first and second locations, respectively, and the first and second waveguides are otherwise free of mechanical contact with the first and second waveguide supports from the first and second locations to the internal cavity of the support structure.

12. The ultrasonic sensor of claim 10 wherein:

the support structure comprises a housing with an internal cavity;

the first and second waveguides are coupled to the ultrasonic transmitter and receiver, respectively within the internal cavity; and the housing comprises a plurality of ventilation perforations.

13. The ultrasonic sensor of claim 10 and further comprising:

a main ultrasonic signal travel path from the ultrasonic transmitter, down the first waveguide to the measurement gap, across the measurement gap from the first waveguide to the second waveguide, and up the second waveguide to the ultrasonic receiver; and a self-test ultrasonic signal travel path from the ultrasonic transmitter, down the first waveguide to the first location, from the first location to the first waveguide support, up the first waveguide support to the support structure, from the support structure to the second waveguide support, down the second waveguide support to the second location, from the second location to the second waveguide, and up the second waveguide to the ultrasonic receiver.

14. An ultrasonic sensor comprising:

a support structure for coupling to a process to be measured and having a process isolated side and a process exposed side;

an ultrasonic transmitter on the process isolated side;

an ultrasonic receiver on the process isolated side;

waveguide means for guiding ultrasonic signals from the ultrasonic transmitter to a measurement gap on the process exposed side and from the measurement gap to the ultrasonic receiver, thus defining a main waveform travel path;

waveguide support means for supporting the waveguide means on the process exposed side and for isolating the process isolated side from the process exposed side; and wherein the waveguide support means is coupled to the waveguide means so as to define a self-test travel path for the ultrasonic signals from the ultrasonic transmitter to the ultrasonic receiver, the self-test travel path being different from and longer than the main waveform travel path.

* * * * *